United States Patent
Leitold et al.

(10) Patent No.: US 10,933,233 B2
(45) Date of Patent: Mar. 2, 2021

(54) PRODUCTION METHOD FOR A RING ELECTRODE

(71) Applicant: Heraeus Deutschland GmbH & Co. KG, Hanau (DE)

(72) Inventors: Christiane Leitold, Hanau (DE); Oliver Keitel, Hanau (DE); Hoang-Minh Le, Hanau (DE); Jörg Krenzer, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 54 days.

(21) Appl. No.: 16/278,275

(22) Filed: Feb. 18, 2019

(65) Prior Publication Data
US 2019/0255317 A1   Aug. 22, 2019

(30) Foreign Application Priority Data
Feb. 21, 2018   (EP) .................... 18157921

(51) Int. Cl.
*A61B 5/00*   (2006.01)
*G16H 40/63*   (2018.01)
(Continued)

(52) U.S. Cl.
CPC ............. *A61N 1/0551* (2013.01); *A61N 1/05* (2013.01); *A61N 1/362* (2013.01);
(Continued)

(58) Field of Classification Search
CPC .... A61N 1/0551; A61N 1/37512; A61N 1/05; A61N 1/36125; A61N 1/362;
(Continued)

(56) References Cited

U.S. PATENT DOCUMENTS

| | | |
|---|---|---|
| 2001/0042297 A1 | 11/2001 | Wolf et al. |
| 2004/0210289 A1* | 10/2004 | Wang ..................... B82Y 25/00 607/116 |

(Continued)

FOREIGN PATENT DOCUMENTS

| | | |
|---|---|---|
| DE | 102012013338 | 5/2014 |
| EP | 0962267 | 12/1999 |
| EP | 3170574 | 5/2017 |

*Primary Examiner* — Michael W Kahelin
*Assistant Examiner* — George E Banis
(74) *Attorney, Agent, or Firm* — Dicke, Billig & Czaja, PLLC

(57) ABSTRACT

One aspect relates to a production method for a ring electrode, to a ring electrode, and to an electrode system. One method for the ring electrode includes providing an outer element, including an outer tube, providing a first inner element, including a first inner tube having a first core of a sacrificial material, providing a second inner element, including a second core of a sacrificial material, forming a composite tube by arranging the first inner element and the second inner element inside the outer element, the first inner element and the second inner element being arranged off-center with respect to one another, drawing the composite tube in a longitudinal direction of the composite tube, separating a composite tube disk from the composite tube, removing the sacrificial material of the first core, and removing the sacrificial material of the second core in order to obtain a contacting opening in the ring electrode.

15 Claims, 6 Drawing Sheets

(51) Int. Cl.
| | |
|---|---|
| A61B 5/11 | (2006.01) |
| A61B 5/0205 | (2006.01) |
| A61B 5/021 | (2006.01) |
| A61B 5/024 | (2006.01) |
| A61N 1/05 | (2006.01) |
| A61N 1/375 | (2006.01) |
| A61N 1/36 | (2006.01) |
| A61N 1/362 | (2006.01) |
| B21C 1/00 | (2006.01) |
| B21C 1/22 | (2006.01) |
| C23F 1/18 | (2006.01) |
| C23F 1/30 | (2006.01) |
| A61B 5/042 | (2006.01) |
| B21C 37/06 | (2006.01) |

(52) U.S. Cl.
CPC ..... *A61N 1/36125* (2013.01); *A61N 1/37512* (2017.08); *B21C 1/003* (2013.01); *B21C 1/22* (2013.01); *C23F 1/18* (2013.01); *C23F 1/30* (2013.01); *A61B 5/042* (2013.01); *A61B 2562/125* (2013.01); *B21C 37/06* (2013.01)

(58) Field of Classification Search
CPC . B21C 1/003; B21C 1/22; B21C 37/06; C23F 1/18; C23F 1/30; A61B 5/042; A61B 2562/125
See application file for complete search history.

(56) References Cited

U.S. PATENT DOCUMENTS

| | | | |
|---|---|---|---|
| 2005/0053472 A1* | 3/2005 | Yagoobi | H02K 44/04 417/48 |
| 2013/0296678 A1* | 11/2013 | Larsen | A61N 1/05 600/373 |
| 2014/0200640 A1 | 7/2014 | Wulfman et al. | |
| 2017/0113034 A1* | 4/2017 | Frericks | A61N 1/0551 |
| 2017/0143220 A1 | 5/2017 | Doerge et al. | |

* cited by examiner

| ⌀AD | 1.5-2 |
| --- | --- |
| ⌀ID | 1.4-1.3 |
| WS | ~0.1 |
| ⌀K | 0.1-0.3 |
| WS2 | 0.05-0.2 |
| WS3 | 0.4-0.7 |
| Material | PtIr10 |

PRODUCTION METHOD FOR A RING ELECTRODE

CROSS-REFERENCE TO RELATED APPLICATION

This Utility Patent Application claims priority to Application No. EP 18 157 921.0 filed on Feb. 21, 2018, which is incorporated herein by reference.

TECHNICAL FIELD

One aspect relates to a production method for a ring electrode, to a corresponding ring electrode, to an electrode system including such a ring electrode and to the use of this ring electrode or of this electrode system in a cardiac pacemaker and/or for neurostimulation. The ring electrode is generally intended for use as or in an active implantable medical device, although it may also be used in other ways. It may be used for signal acquisition and/or for stimulation.

BACKGROUND

The typically very small component size of a ring electrode for an active implantable medical device and the even smaller dimensions of its partial features require very expensive and elaborate production installations and production methods with many individual working steps. Conventionally, ring electrodes are produced by machining, for instance turning from a material in the form of a rod, and the excess material inside the ring is removed, for example, by spark erosion. The ring electrodes are often made of noble metal, for example from platinum alloys, so that the machining and the removal of the excess material lead to significant noble metal losses and cost disadvantages.

For these and other reasons, a need exists for the present embodiments.

SUMMARY

One aspect is a ring electrode with an outer element, a first inner element, and a second inner element. The outer element has an outer tube and the first inner element and the second inner element are arranged inside the outer element, and the first inner element and the second inner element are arranged off-center with respect to one another, in order to form a composite tube. The outer element, the first inner element and the second inner element are drawn together in a longitudinal direction of the composite tube. The first inner element has a first inner tube, which encloses a first cavity from which a sacrificial material has been removed. The second inner element encloses a second cavity from which a sacrificial material has been removed, and which forms a contacting opening in the ring electrode.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
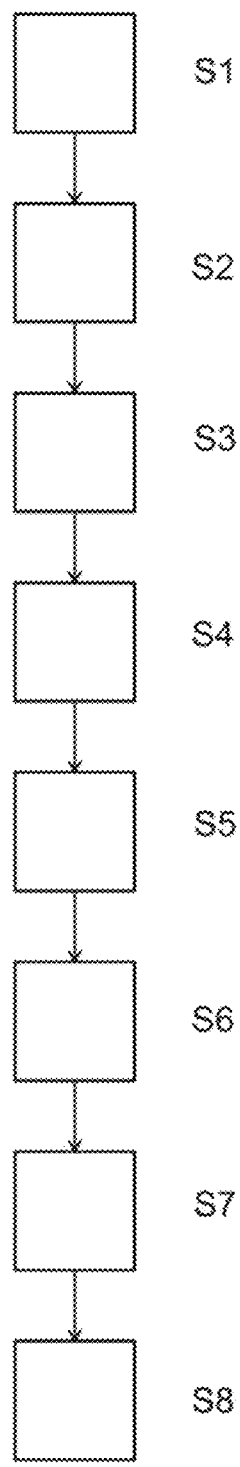
FIG. 1 illustrates a production method for a ring electrode.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

One embodiment provides a production method for a ring electrode, and such a ring electrode, which are less cost-intensive.

One embodiment is a production method for a ring electrode, a corresponding ring electrode, an electrode system including such a ring electrode, and the use of this ring electrode or of this electrode system, according to the features of the independent claims. Embodiments and refinements may be found in the dependent claims and the following description.

One embodiment provides a production method for a ring electrode that includes the following steps (not necessarily in this order):

providing an outer element, which includes an outer tube,
providing a first inner element, which includes a first inner tube having a first core of a sacrificial material,
providing a second inner element, which includes a second core of a sacrificial material,
forming a composite tube by arranging the first inner element and the second inner element inside the outer element, the first inner element and the second inner element being arranged off-center with respect to one another,
drawing the composite tube in a longitudinal direction of the composite tube,
separating a composite tube disk from the composite tube,
removing the sacrificial material of the first core, and
removing the sacrificial material of the second core in order to obtain a contacting opening in the ring electrode.

An advantage of one embodiment is that the ring electrode is not produced from a solid, for example from a rod material, but directly from hollow tubes. In this way, machining or erosive processing of the outer diameter of the tubes can be obviated, and much less noble metal is used inside the ring electrode and lost, since the tubes do not have a noble metal core that needs to be removed. Not only the costs and the outlay for the machining and the removal, but also the costs of the noble metal and of the noble metal losses are therefore avoided.

The contacting opening in the ring electrode may be used for electrical and/or for mechanical contacting with a conductor element. The contacting opening may therefore be used as an electrical connection element and/or as a mechanical fastening element for the conductor element. The conductor element may be a cable or a wire for contacting the ring electrode with a medical device, such as a cardiac pacemaker.

The composite tube may be produced by inserting the first inner element and the second inner element into the outer element. In this case, a defined interface with, for example, a defined material condition may be produced between the outer element, the first inner element and/or the second inner element. Thus, for example, a defined material condition of the interface of the contacting opening for the conductor element may be provided, so that the contacting of the conductor element on the ring electrode, for example by crimping, clamping or insertion, can be particularly reliable and reproducible.

The off-center arrangement of the first inner element and the second inner element with respect to one another may be understood as meaning that the midpoints or centroids of the two inner elements do not lie on one another in cross section. The first inner element and the second inner element are thus not arranged concentrically, and therefore do not form the shape of a target ring. One inner element may at least partially cover the other inner element, and the two inner elements lie next to one another, but they do not have a common midpoint or centroid in cross section. In this way, the contacting opening may be formed in such a way that, as seen in cross section, it lies outside the midpoint of the ring electrode.

Drawing or pulling may be understood as tensile pressure deformation during which an initial wire is brought to a reduced diameter by a drawing nozzle, drawing block or die in a plurality of steps. During the drawing of the composite tube, the outer and inner elements may flow together, and reduce or possibly even close free spaces between them. The first inner tube may, for example, flow around the second inner element in such a way that the second inner element protrudes into the first inner tube in the shape of a nose.

By the drawing, a form fit and/or a force fit may at least partially be achieved between the individual components of the composite tube, so that a final geometry of the ring electrode after the present production method is stable. This may be understood as meaning that the individual components of the composite tube hold against one another by mutual mechanical blocking and/or friction. By the drawing, a material fit may also be achieved at least partially, for example by cold welding of the individual components of the composite tube. This may be understood as meaning that the individual components of the composite tube hold against one another by chemical or atomic bonding.

In one embodiment, the outer element and the first inner element are arranged concentrically with one another. This may be understood as meaning that the midpoints or centroids of the outer element and of the first inner element lie on one another in cross section. In this way, a cylindrical main opening of the ring electrode can be formed.

In one embodiment, the diameter of the first inner element is greater than the diameter of the second inner element. In one embodiment, the diameter of the first inner element is more than two times as great as the diameter of the second inner element. In one embodiment, the diameter of the first inner element is more than three times as great as the diameter of the second inner element. In this way, the main opening, formed by the first inner element, of the ring electrode is significantly larger than the contacting opening formed by the second inner element.

In one embodiment, the removal of the sacrificial material of the first core includes corrosion or etching. In one embodiment, the removal of the sacrificial material of the second core includes corrosion or etching. The removal of the sacrificial material of the first core and the removal of the sacrificial material of the second core may be carried out by the same or a different type of corrosion or etching. Corrosion may be understood as being the treatment of the ring electrode or of its components by means of a corrosive fluid. Aggressive chemicals such as acids or alkalis may be used as corrosive fluids. Etching may be understood as the ablation of material of the ring electrode or of its components by applying an etchant. Chemical substances which modify (usually oxidize) the material to be etched in a chemical reaction, and thus bring it into solution, may be used as etchants. Etchants may be acids or strong oxidizing agents. The corrosion or etching may be assisted by ultrasound, heat and/or electrical current.

In one embodiment, the removal of the sacrificial material of the first core is carried out with the aid of an acid. In one embodiment, the removal of the sacrificial material of the second core is carried out with the aid of an acid. In both cases, the same acid may, but need not, be used. The acid may be nitric acid, hydrochloric acid, hydrogen peroxide and/or the like.

In one embodiment, the second inner element includes a second inner tube, which contains the second core. The second inner tube may flow into free spaces between the outer tube and the first inner tube during the drawing of the composite tube. The second inner tube and/or the first inner tube may be soft-annealed in order to promote this flow.

In one embodiment, the outer tube includes a noble metal or a noble metal alloy. In one embodiment, the first inner tube includes a noble metal or a noble metal alloy. In one embodiment, the optional second inner tube includes a noble metal or a noble metal alloy. The outer tube, the first inner tube and/or the second inner tube may be made of the same material or different materials. Noble metals may be understood as meaning metals whose redox pairs have a positive standard potential with respect to the standard hydrogen electrode. The noble metal may be platinum or the like. The noble metal alloy may be a platinum-iridium alloy or the like, and for example, a PtIr10 alloy.

In one embodiment, the sacrificial material of the first core is less noble than the material of the first inner tube. In one embodiment, the sacrificial material of the second core is less noble than the material of the first and/or second inner tube. Base metals or non-noble metals may be understood as meaning metals whose redox pairs have a negative standard potential with respect to the standard hydrogen electrode.

In one embodiment, the first core of sacrificial material includes a non-noble metal or a non-noble metal alloy. In one embodiment, the second core of sacrificial material includes a non-noble metal or a non-noble metal alloy. A non-noble metal alloy may be understood as meaning an alloy of one or more non-noble metals or base metals. The sacrificial material of the first core and the sacrificial material of the second core may be made of the same material or different materials. The non-noble metal alloy may be made of or include copper, a nickel-cobalt-based alloy or the like. For better geometrical stability of the (smaller) opening to be produced, the sacrificial material of the second core may be harder than the sacrificial material of the first core. In one embodiment, the first core is made of copper. In one embodiment, the second core is made of a nickel-cobalt-based alloy. The nickel-cobalt-based alloy may be MP35N (35% Ni, 35% Co, 20% Cr and 10% Mo) or MP35NLT.

The outer element, all the inner elements and/or all the sacrificial materials may also consist of plastics, ceramics or cermets. The material pairings may be selected in any desired way such that the sacrificial material can be removed more easily with respect to the surrounding inner element.

In one embodiment, the drawing of the composite tube is carried out with a deformation factor of between 3 and 25% per individual drawing, and in one embodiment with a deformation factor of between 3 and 17% per individual drawing. In the overall composite after a plurality or all of the drawings the deformation factor may lie between 50 and 185%. A deformation factor or shaping factor may be understood as meaning the logarithmic ratio of the length of a sample after the deformation to a length of the sample before the deformation.

In one embodiment, the outer tube and/or one or all of the inner tubes are soft-annealed before the drawing in order to promote flow of the individual tubes into free spaces between the individual tubes.

In one embodiment, the production method includes cutting of the composite tube into rings after the removal of the sacrificial materials. The cutting may be carried out contactlessly, for example by wire erosion. For the cutting, the composite tube may be fixed with a clamping device and, for example, fastened on a strip.

In one embodiment, after the removal of the sacrificial materials and either before or after the cutting of the composite tube into rings, the production method includes further processing which, as seen in a longitudinal section through the ring electrode, reduces the second inner element in length in relation to the outer element and/or the first inner element, so that the second inner element does not extend along the entire length of the outer element and/or of the first inner element in longitudinal section. In other words, the second inner element, or the contacting opening, forms at least one step in the ring electrode. This may be done by mechanical processing and/or an erosion method.

In one embodiment, before the removal of the sacrificial materials, the production method does not include a heat treatment, and for example, does not include a recrystallization anneal. This has the advantage in one embodiment that diffusion between the sacrificial materials and the inner elements can be avoided. A recrystallization anneal may be understood as meaning an anneal without a phase change at a temperature in the recrystallization range after cold forming, for example the drawing. After the removal of the sacrificial materials, a heat treatment, and for example, a recrystallization anneal, may be provided in order for example to increase the ductility of the ring electrode.

The outer element and all the inner elements may have any desired shapes in cross section, and may, for example, be circular, oval, elliptical, semicircular, but also square, rectangular, polygonal or the like. The outer element and all the inner elements may have different cross sections to one another. In one embodiment, the outer element and all the inner elements are circular in cross section.

In one embodiment, the outer tube and/or one or all of the inner tubes is a profiled tube. A profiled tube may be understood as meaning a tube which has a non-circular cross section, for example a square, rectangular, semicircular or arced shape in cross section. In one embodiment, the first inner tube is a profiled tube. The inner tube may in this case for the most part be circular, but at least one position have an arced protuberance which is configured in order to receive the second inner element. The profiled tube may also have an arced protuberance for a further inner element at a different position. The protuberance of the profiled tube may also be trapezoidal.

By the production method according to one embodiment, any desired numbers and arrangements of openings may be produced in a ring electrode. By the removal of the sacrificial material of the first core, a through-opening may be produced in the ring electrode. By the removal of the sacrificial material of the second core, a contacting opening for electrical and/or mechanical contacting may be produced. By the removal of a sacrificial material of an optional third core, a further opening may be produced in the ring. In one embodiment, to this end the production method furthermore includes the following steps:

providing a third inner element, which includes a third core of a sacrificial material, forming the composite tube by arranging the third inner element inside the outer element, the first, second and third inner elements being arranged off-center with respect to one another, and removing the sacrificial material of the third core.

The third inner element may have a third inner tube, which contains the third core of sacrificial material. The sacrificial material of the third core may be removed as described above by corrosion or etching. The further opening, provided by the removal of the third core, of the ring electrode may be arranged on the outer circumference of the first inner tube, opposite the contacting opening provided by removal of the second core. The through-opening, provided by the removal of the first core, of the ring electrode may be configured in an apple shape so that the contacting opening and the further opening may respectively be arranged in the opposite protrusions of the apple-shaped through-opening on the outer circumference of the contacting opening.

It is furthermore proposed to provide a ring electrode which includes an outer element, a first inner element and a second inner element. The outer element includes an outer tube. The first inner element and the second inner element are arranged inside the outer element. The first inner element and the second inner element are arranged off-center with respect to one another, in order to form a composite tube. The outer element, the first inner element and the second inner element have been drawn together in a longitudinal direction of the composite tube. The first inner element has a first inner tube, which encloses a first cavity from which a sacrificial material has been removed. The second inner element encloses a second cavity from which a sacrificial material has been removed, and which forms a contacting opening in the ring electrode.

In one embodiment, the ring electrode, as seen in a cross section, has a boundary line, interface or "seam" between the outer element and the first inner element. This may be understood as meaning that the outer element and the first inner element do not fully merge into one another and fuse with one another, but rather under the microscope the two elements can still be seen as originally different components.

Some possible dimensions of the ring electrode will be mentioned below. The individual dimensions are to be understood independently of one another and do not necessarily form a common embodiment, although this is possible. An outer diameter of the ring electrode, and therefore an outer diameter of the outer element of the outer tube, may lie between 1 and 3 mm, in one embodiment between 1.3 and 2.5 mm and in one embodiment between 1.5 and 2.0 mm. An inner diameter of the first inner element, and therefore an inner diameter of the first inner tube, may lie between 0.9 and 2.9 mm, in one embodiment between 1.2 and 2.4 mm, and in one embodiment between 1.4 and 1.9 mm. An inner diameter of the contacting opening, and therefore an outer diameter of the second core, may lie between 0.10 and 0.30 mm, in one embodiment between 0.15 and 0.25 mm, in one embodiment between 0.17 and 0.20 mm.

It is furthermore proposed to provide an electrode system which includes such a ring electrode and a conductor element. The conductor element is connected to a contacting opening in the ring electrode. The conductor element may be a wire, a cable or the like. The contacting opening in the ring electrode may be a type of small inner hole for electrical and/or mechanical contacting of the conductor element. The contacting opening may therefore be a fastening element for the conductor element. The conductor element may be connected to the contacting opening, or to the fastening element of the ring electrode, by welding, for example, laser welding or resistance welding, soldering, crimping or the like. In this way, particularly secure and simple fastening of the conductor element on the ring electrode is achieved.

It is furthermore proposed to use such a ring electrode or such an electrode system, which has been produced according to the production method described here, in a cardiac pacemaker or for neurostimulation. One embodiment may be used as for stimulation or measuring electrode for cardiac pacemaker electrodes, for example, for ventricular, atrial and left-ventricular leads. One embodiment may also be used for neurostimulation, for example in spinal cord stimulation or deep brain stimulation. Use on catheters, for example in electrophysiology applications, is furthermore possible, for example for ablation, ECG measurement or the like. Naturally, further possible uses are also possible.

FIG. 1 illustrates a production method for a ring electrode 10. The ring electrode 10 may be used as an active implantable medical device, for example in a cardiac pacemaker or for neurostimulation. It may be used for signal acquisition and for stimulation.

The production method for the ring electrode 10 includes the following steps (not necessarily in this order):

In a step S1, providing an outer element 11, which includes an outer tube 12.

In a step S2 providing a first inner element 13, which includes a first inner tube 14 having a first core 15 of a sacrificial material.

In a step S3, providing a second inner element 16, which includes a second core 17 of a sacrificial material.

In a step S4, forming a composite tube by arranging the first inner element 13 and the second inner element 16 inside the outer element 11, the first inner element 13 and the second inner element 16 being arranged off-center with respect to one another.

In a step S5, drawing the composite tube in a longitudinal direction of the composite tube.

In a step S6, separating a composite tube disk from the composite tube.

In a step S7, removing the sacrificial material of the first core 15, in order to obtain a ring electrode 10.

In a step S8, removing the sacrificial material of the second core 17, in order to obtain a contacting opening 2 in the ring electrode 10.

FIGS. 2A to 2E illustrate plan views of a plurality of embodiments of a precursor of the ring electrode 10 after step S4, that is, after the formation of the composite tube, but before step S5, the drawing of the composite tube. The precursor of the ring electrode 10 includes an outer element 11, a first inner element 13 and a second inner element 16.

Figure 2A:
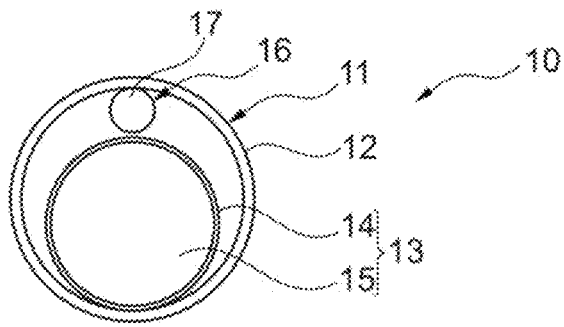
FIGS. 2A-E illustrate a plurality of embodiments of a step of the production method for a ring electrode.

In the embodiment illustrated in FIG. 2A, the outer element 11 is circular and includes a circular outer tube 12. The first inner element 13 and the second inner element 16 are likewise circular and lie inside the outer element 11 and its outer tube 12. The first inner element 13 and the second inner element 16 are arranged off-center with respect to one another, that is, the midpoints of the two inner elements do not lie on one another. The diameter of the first inner element 13 is significantly greater than the diameter of second inner element 16.

The first inner element 13 has a circular first inner tube 14, which encloses a likewise circular first cavity, which includes a first sacrificial material. The second inner element 16 encloses a circular second cavity, which includes a second sacrificial material.

The outer tube 12 and the first inner tube 13 consist in this case of the alloy PtIr10. The first core 15 consists in this case of copper. The second core 17 consists in this case of MP35N. By the removal of the sacrificial material of the first core 15, in the subsequent production step S7 a through-opening 3 can be produced in the ring electrode 10. The step S7 may be corrosion with nitric acid in an ultrasound bath at 80° C. By the removal of the sacrificial material of the second core 17, in the subsequent production step S8 a contacting opening 2 for electrical and/or mechanical contacting can be produced. Step S8 may be corrosion with HCl and $H_2O_2$ in the ratio 3:1 for 15 minutes in an ultrasound bath at 80° C. The contacting opening 2 may be used as an electrical connection element and/or as a mechanical fastening element for a conductor element, in order to form an electrode system from the ring electrode 10 and the conductor element.

Figure 2B:
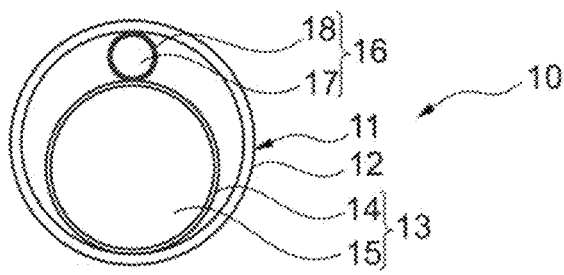

In the embodiment illustrated in FIG. 2B, the second inner element 16 includes a second inner tube 18, which includes the second core 17. The second inner tube 18 may flow into free spaces between the outer tube 12 and the first inner tube 13 during the drawing of the composite tube. The second inner tube 18 in this case likewise consists of PtIr10.

Figure 2C:
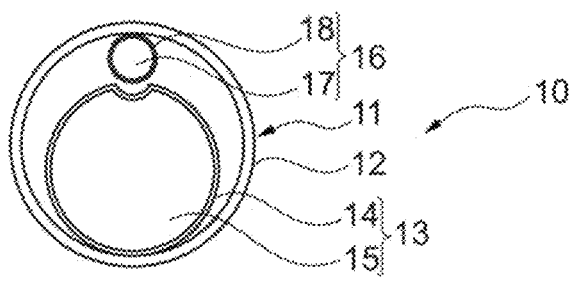
Figure 2D:
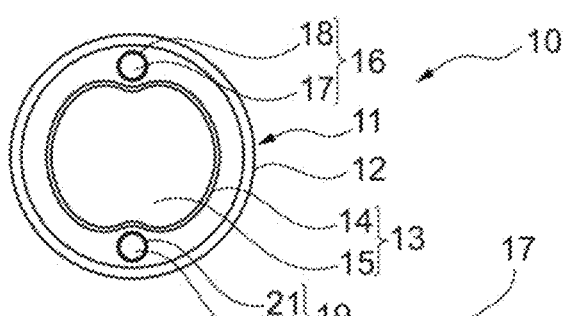
Figure 2E:
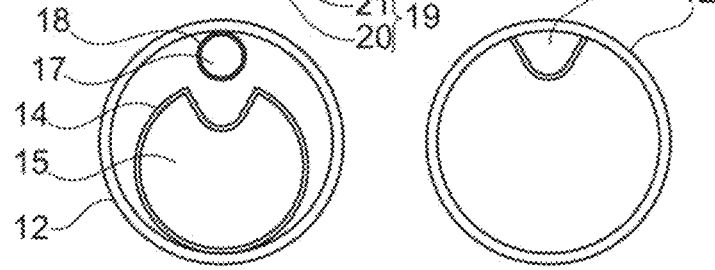

In the embodiments illustrated in FIGS. 2C to 2E, the first inner tube 13 is a profile tube. The inner tube 13 is for the most part circular, but in the embodiments illustrated in FIGS. 2c and 2e has an arced (FIG. 2c) or trapezoidal (FIG. 2e) protrusion at one position in order to receive the second inner element 16.

In the embodiment illustrated in FIG. 2D, the profiled tube of the first inner tube 13 has an arced protrusion for a further, third inner element 19 at a further position opposite the second inner element 16. The third inner element 19 lies inside the outer element 11, and the first, second and third inner elements are arranged off-center with respect to one another. The third inner element 19 includes a third inner tube 21 and a third core 20 of a sacrificial material, by the removal of which a further opening can be produced in the ring electrode 10. In the embodiment illustrated in FIG. 2d, an apple-shaped through-opening 3 of the ring electrode 10 is provided by the removal of the first core 15, in which electrode the contacting opening 2 and the further opening are respectively arranged in the opposite protrusions of the apple-shaped through-opening 3.

Figure 3A:
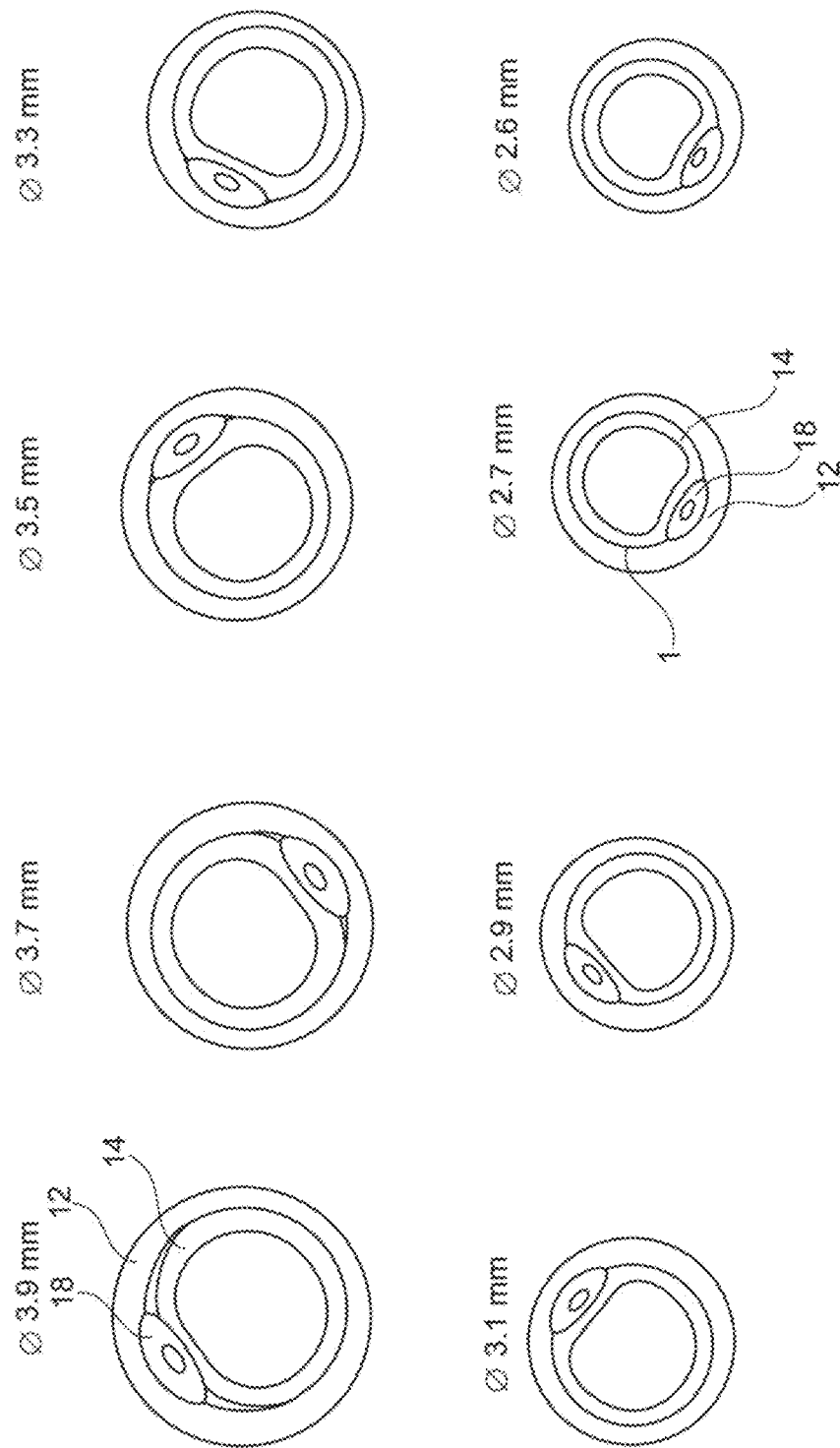
FIGS. 3A-3B illustrate a plurality of substeps of a further step of the production method for a ring electrode.
Figure 3B:
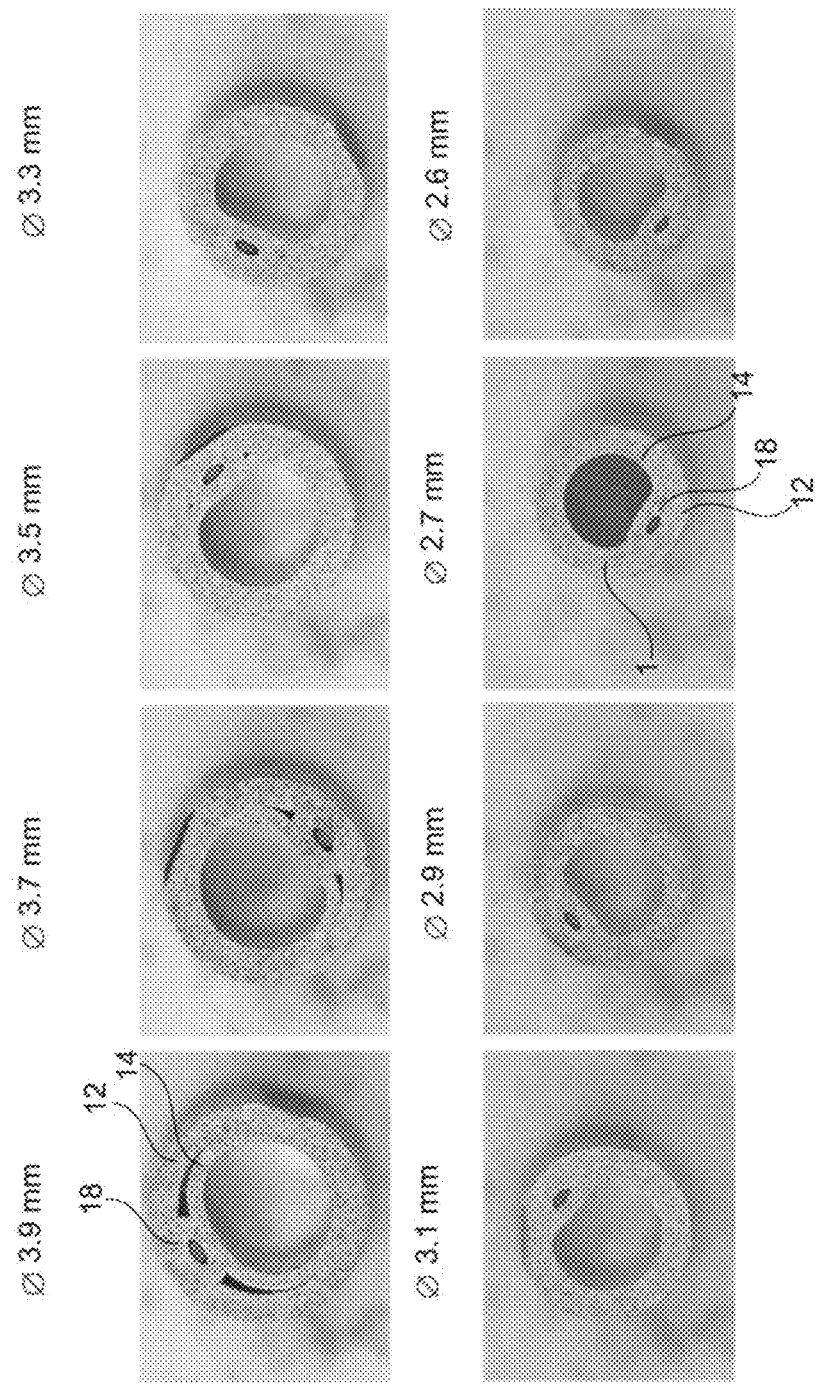

FIGS. 3A and 3B illustrate plan views of the ring electrode 10 after a plurality of substeps of the drawing of the composite tube in the longitudinal direction as photographs and figures. The drawing of the composite tube may be carried out according to the following drawing sequence to the following diameters.

| Drawing sequence Ø [mm] |
| --- |
| 5 |
| 4.9 |
| 4.8 |
| 4.7 |
| 4.6 |
| 4.5 |
| 4.4 |
| 4.3 |
| 4.2 |
| 4.1 |
| 4 |
| 3.9 |
| 3.8 |
| 3.7 |
| 3.6 |
| 3.5 |
| 3.4 |
| 3.3 |
| 3.2 |
| 3.1 |
| 3 |
| 2.9 |
| 2.8 |
| 2.7 |
| 2.6 |

FIG. 3 illustrates the ring electrode 10 with decreasing diameters. The fusion or flowing together of the outer tube 12 and of the first inner tube 14 can be seen. The free spaces or cavities between these two elements decrease more and more. Only a boundary line 1 remains visible between the outer element 11 and the first inner element 13.

Figures 4A, 4B:
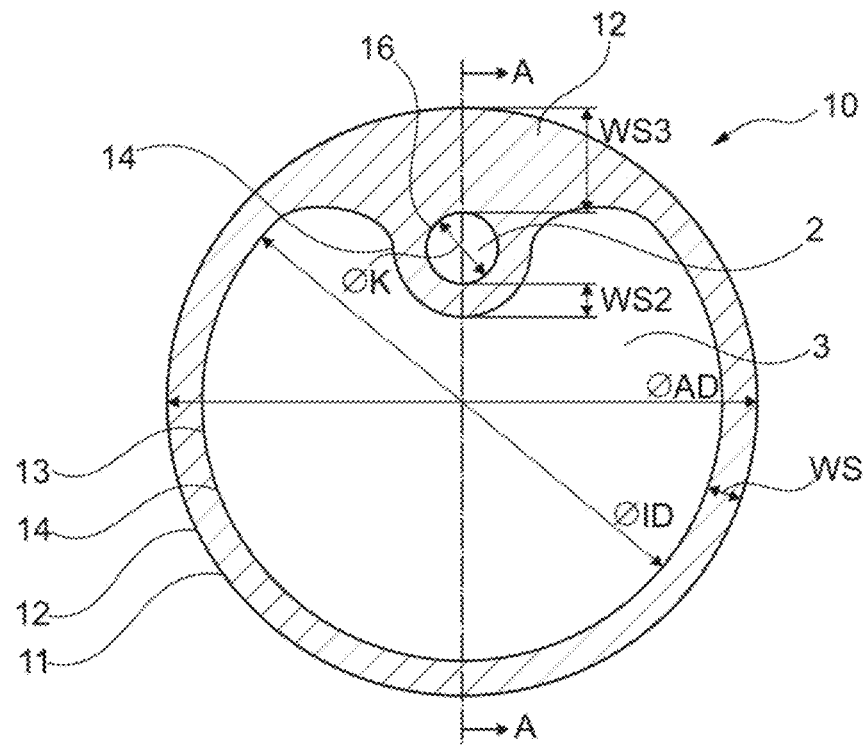
FIGS. 4A-4B illustrate a ring electrode in a plan view and exemplary dimensions of the ring electrode.

FIG. 4A illustrates a ring electrode 10 in a plan view, and FIG. 4B illustrates three exemplary dimensions of the ring electrode 10 according to FIG. 4a in millimeters. The ring electrode 10 includes an outer element 11 having an outer tube 12, and a first inner element 13 having a first inner tube 14. The outer tube 12 and the first inner tube 14 have merged into one another. Arranged off-center with respect to the first inner tube 14, there is a significantly smaller second inner element 16, around which the first inner tube 14 flows. The first inner tube 14 forms a through-opening 3, and the second inner element 16 forms a contacting opening 2 for the ring electrode 10. The contacting opening 2 partially enclosed by the first inner tube 14 protrudes in the shape of a nose into the through-opening 3 of the ring electrode 10.

Figure 5A:
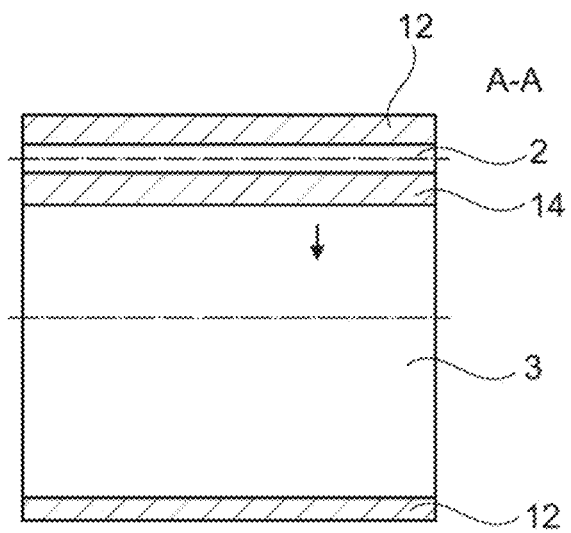
FIGS. 5A-5B illustrate exemplary longitudinal sections through a ring electrode.
Figure 5B:
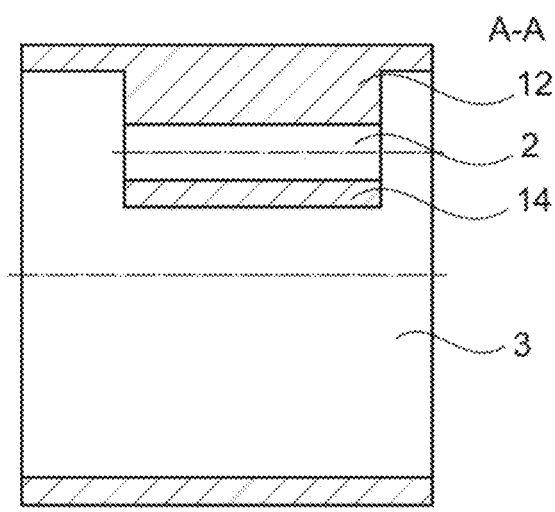

FIGS. 5A and 5B illustrate exemplary longitudinal sections through a longitudinal direction of the ring electrode 10 according to FIG. 4. FIG. 5a illustrates a ring electrode 10 having a constant inner diameter. FIG. 5b illustrates a ring electrode 10 having an asymmetrical and step-shaped inner diameter. The second inner element 16 is reduced in length compared with the outer element 11, so that the second inner element 16, and therefore the contacting opening 2, does not extend along the entire length of the outer element 11 in longitudinal section. In the ring electrode 10 illustrated in FIG. 5b, the contacting opening 2 terminates at both its ends inside the outer element 11 of the ring electrode 10, that is, the contacting opening 2 does not terminate flush with the ring electrode 10 at either end.

In addition, it is to be pointed out that "comprising" does not exclude any other elements or steps, and "a" or "one" does not exclude a multiplicity. Furthermore, it is to be pointed out that features or steps which have been described in reference to one of the exemplary embodiments above may also be used in combination with other features or steps of other exemplary embodiments described above. References in the claims are not to be regarded as restrictive.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof

What is claimed is:

1. A production method for a ring electrode, comprising:
providing an outer element, which comprises an outer tube;
providing a first inner element, which comprises a first inner tube having a first core of a sacrificial material;
providing a second inner element, which comprises a second core of a sacrificial material;
forming a composite tube by arranging the first inner element and the second inner element inside the outer element, the first inner element and the second inner element being arranged off-center with respect to one another;
drawing the composite tube in a longitudinal direction of the composite tube;
separating a composite tube disk from the composite tube;
removing the sacrificial material of the first core; and
removing the sacrificial material of the second core in order to obtain a contacting opening in the ring electrode.

2. The method of claim 1, wherein the removal of the sacrificial material of the first core and/or of the sacrificial material of the second core is corrosion or etching.

3. The method of claim 1, wherein the removal of the sacrificial material of the first core and/or of the sacrificial material of the second core is carried out with the aid of an acid comprising nitric acid, hydrochloric acid and/or hydrogen peroxide.

4. The method of claim 1, wherein the sacrificial material of the first core and/or the sacrificial material of the second core is less noble than the material of the outer tube and/or of the first inner tube.

5. The method of claim 1, wherein the outer tube and/or the first inner tube comprises one of a noble metal, a noble metal alloy, and a platinum-iridium alloy.

6. The method of claim 1, wherein the first core of sacrificial material and/or the second core of sacrificial material comprises a non-noble metal alloy, and copper and/or MP35N.

7. The method of claim 1, wherein the drawing of the composite tube is carried out with a deformation factor of between 3 and 25% per individual drawing.

8. The method of claim 1, wherein the diameter of the first inner element is greater than the diameter of the second inner element.

9. The method of claim 1, wherein the second inner element comprises a second inner tube, which encloses the second core.

10. The method of claim 1 further comprising:
providing a third inner element, which comprises a third core of a sacrificial material;
forming the composite tube by arranging the third inner element inside the outer element, the first, second and third inner elements being arranged off-center with respect to one another; and
removing the sacrificial material of the third core.

11. The method of claim 1, wherein the production method does not comprise a recrystallization method.

12. A ring electrode, comprising:
an outer element;
a first inner element; and
a second inner element;
wherein the outer element comprises an outer tube;
wherein the first inner element and the second inner element are arranged inside the outer element, and the first inner element and the second inner element are arranged off-center with respect to one another, in order to form a composite tube;
wherein the outer element, the first inner element and the second inner element are drawn together in a longitudinal direction of the composite tube;
wherein the first inner element has a first inner tube, which encloses a first cavity from which a sacrificial material has been removed; and
wherein the second inner element encloses a second cavity from which a sacrificial material has been removed, and which forms a contacting opening in the ring electrode.

13. The ring electrode of claim 12, wherein the ring electrode, as seen in a cross section, has a boundary line between the outer element and the first inner element.

14. The ring electrode of claim 12 configured in an electrode system and further comprising a conductor element, wherein the conductor element is connected to a contacting opening in the ring electrode.

15. The ring electrode of claim 12 configured in a cardiac pacemaker and/or for neurostimulation.

* * * * *